United States Patent
Mitsuhashi

(10) Patent No.: US 8,830,310 B2
(45) Date of Patent: Sep. 9, 2014

(54) CAPSULE ENDOSCOPE

(71) Applicant: Olympus Medical Systems Corp., Tokyo (JP)

(72) Inventor: Kei Mitsuhashi, Nishitokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/900,599

(22) Filed: May 23, 2013

(65) Prior Publication Data

US 2013/0314518 A1    Nov. 28, 2013

Related U.S. Application Data

(63) Continuation of application No. PCT/JP2011/079065, filed on Dec. 15, 2011.

(30) Foreign Application Priority Data

Jan. 20, 2011   (JP) .................................. 2011-009971

(51) Int. Cl.
    *H04N 5/235*      (2006.01)
    *A61B 1/04*      (2006.01)
    *A61B 1/00*      (2006.01)
    *A61B 1/06*      (2006.01)

(52) U.S. Cl.
    CPC ............ *H04N 5/2354* (2013.01); *A61B 1/0684* (2013.01); *A61B 1/041* (2013.01); *A61B 1/00009* (2013.01)
    USPC ............................................ 348/68; 600/109

(58) Field of Classification Search
    USPC ......................................................... 348/68
    See application file for complete search history.

(56) References Cited

U.S. PATENT DOCUMENTS

| | | | | |
|---|---|---|---|---|
| 8,133,169 B2* | 3/2012 | Nagase et al. | ................. | 600/117 |
| 8,529,441 B2* | 9/2013 | Bandy et al. | .................. | 600/173 |
| 8,536,667 B2* | 9/2013 | de Graff et al. | ............... | 257/419 |
| 8,629,916 B2* | 1/2014 | Tanaka | ........................ | 348/222.1 |
| 2006/0184039 A1* | 8/2006 | Avni et al. | ..................... | 600/476 |

(Continued)

FOREIGN PATENT DOCUMENTS

| | | | |
|---|---|---|---|
| JP | 2006-524097 A | 10/2006 | |
| JP | 2009-279172 A | 12/2009 | |

(Continued)

OTHER PUBLICATIONS

International Search Report from related PCT/JP2011/079065 dated Mar. 13, 2012.

*Primary Examiner* — Sath V Perungavoor
*Assistant Examiner* — Howard D Brown, Jr.
(74) *Attorney, Agent, or Firm* — Scully, Scott, Murphy & Presser, P.C.

(57) ABSTRACT

A capsule endoscope includes: a light emitting unit; an imaging unit; an image signal processing unit; and a setting unit that controls the light emitting unit and the imaging unit to perform pre-exposure, measures at least one of a light emission time and a light emission intensity, sets the measured time or intensity for a main exposure process when the measured time or intensity is within a predetermined acceptable range, and sets at least one of the preset light emission time and light emission intensity for the main exposure process when the measured time or intensity is out of the acceptable range, wherein an acquisition process of an image is performed in accordance with the set light emission time or the set light emission intensity.

3 Claims, 11 Drawing Sheets

(56) References Cited

U.S. PATENT DOCUMENTS

| | | | |
|---|---|---|---|
| 2007/0225560 A1* | 9/2007 | Avni et al. | 600/118 |
| 2009/0192351 A1* | 7/2009 | Nishino | 600/109 |
| 2009/0289200 A1* | 11/2009 | Ishii | 250/459.1 |
| 2012/0253200 A1* | 10/2012 | Stolka et al. | 600/459 |
| 2014/0128675 A1* | 5/2014 | Wilson | 600/109 |

FOREIGN PATENT DOCUMENTS

| | | |
|---|---|---|
| JP | 2010-5129 A | 1/2010 |
| JP | 2010-17231 A | 1/2010 |
| JP | 2010-107752 A | 5/2010 |
| JP | 2010-136314 A | 6/2010 |

* cited by examiner

| P | | | |
|---|---|---|---|
| 0 MAGNIFI-CATIONS | 18 MAGNIFI-CATIONS | 12 MAGNIFI-CATIONS | 6 MAGNIFI-CATIONS |
| 6 MAGNIFI-CATIONS | 0 MAGNIFI-CATIONS | 18 MAGNIFI-CATIONS | 12 MAGNIFI-CATIONS |
| 12 MAGNIFI-CATIONS | 6 MAGNIFI-CATIONS | 0 MAGNIFI-CATIONS | 18 MAGNIFI-CATIONS |
| 18 MAGNIFI-CATIONS | 12 MAGNIFI-CATIONS | 6 MAGNIFI-CATIONS | 0 MAGNIFI-CATIONS |

US 8,830,310 B2

CAPSULE ENDOSCOPE

CROSS REFERENCES TO RELATED APPLICATIONS

This application is a continuation of PCT international application Ser. No. PCT/JP2011/079065 filed on Dec. 15, 2011 which designates the United States, incorporated herein by reference, and which claims the benefit of priority from Japanese Patent Applications No. 2011-009971, filed on Jan. 20, 2011, incorporated herein by reference.

BACKGROUND OF THE INVENTION

1. Field of the Invention

The present invention relates to a capsule endoscope to be introduced into a living body.

2. Description of the Related Art

Conventionally, in the field of endoscopes, a capsule endoscope that is a swallow-type endoscope having an imaging function and a radio communication function in a capsule-shaped casing appears, and an endoscope system that introduces the capsule endoscope into an organ of a subject and displays an acquired internal image of the organ (hereinafter, referred to as an in-vivo image) is proposed. The capsule endoscope is orally ingested into the subject to observe the insides of organs of the subject such as a patient, then moves in the organs by peristaltic motion or the like, and finally, is discharged outside the subject. The capsule endoscope captures in-vivo images in a period until the capsule endoscope is discharged outside the subject after it is orally ingested into the subject, for example, at an interval of 0.5 seconds, and wirelessly transmits the obtained in-vivo images sequentially to the outside of the subject.

The in-vivo images wirelessly transmitted in time series by such a capsule endoscope are sequentially received by a receiving device outside the subject. The receiving device stores a group of the in-vivo images received in time series from the capsule endoscope, in a recording medium inserted in advance. The recording medium in the receiving device sufficiently accumulates the group of the in-vivo images obtained by the capsule endoscope, then is removed from the receiving device, and is inserted into an image display device. The image display device receives the group of the in-vivo images in the inserted recording medium, and sequentially displays the obtained in-vivo images on a display. A user such as a doctor or a nurse observes the in-vivo images sequentially displayed on the image display device, and thus can observe (examine) the insides of the organs of the subject through the observation of the in-vivo images.

In order to capture images in a living body, the capsule endoscope is provided with an illumination device such as an LED, an optical system such as a condenser lens, and a solid state image sensor such as a CCD sensor or a CMOS sensor. In the conventional capsule endoscope, a brightness value in a previous frame period is calculated, a light emission time in the next frame period is determined such that a difference between the calculated brightness value and a target brightness value corresponding to brightness suitable for observation becomes small, and thus it is possible to acquire an image having brightness suitable for observation (for example, see Japanese Laid-open Patent Publication No 2010-5129).

SUMMARY OF THE INVENTION

According to one aspect of the present invention, a capsule endoscope which is introduced into a living body, includes: a light emitting unit that emits light; an imaging unit that has a plurality of pixels outputting image signals at an output level corresponding to a light reception value and captures an image; an image signal processing unit that processes the image signals output from the imaging unit; and a setting unit that controls the light emitting unit and the imaging unit to perform pre-exposure of a part of the plurality of pixels before a main exposure process for image acquisition in a frame period set to acquire one image, measures at least one of a light emission time and a light emission intensity about the pre-exposure, sets at least one of the light emission time and the light emission intensity obtained by the pre-exposure as at least one of a light emission time and a light emission intensity in the main exposure process when at least one of the light emission time and the light emission intensity about the pre-exposure is within a preset acceptable range, and sets at least one of the preset light emission time and light emission intensity as at least one of the light emission time and the light emission intensity in the main exposure process when at least one of the light emission time and the light emission intensity obtained by the pre-exposure is out of the preset acceptable range, wherein at least one of the light emitting unit and the image signal processing unit performs a process related to an acquisition process of the image acquired in the frame period, in accordance with the at least one of the light emission time and the light emission intensity set by the setting unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, preferred embodiments of a capsule endoscope according to the invention will be described in detail with reference to the drawings. In addition, the invention is not limited by the embodiments. In addition, in the description of the drawings, the same numerals and signs are given to the same parts.

First Embodiment

Figure 1:
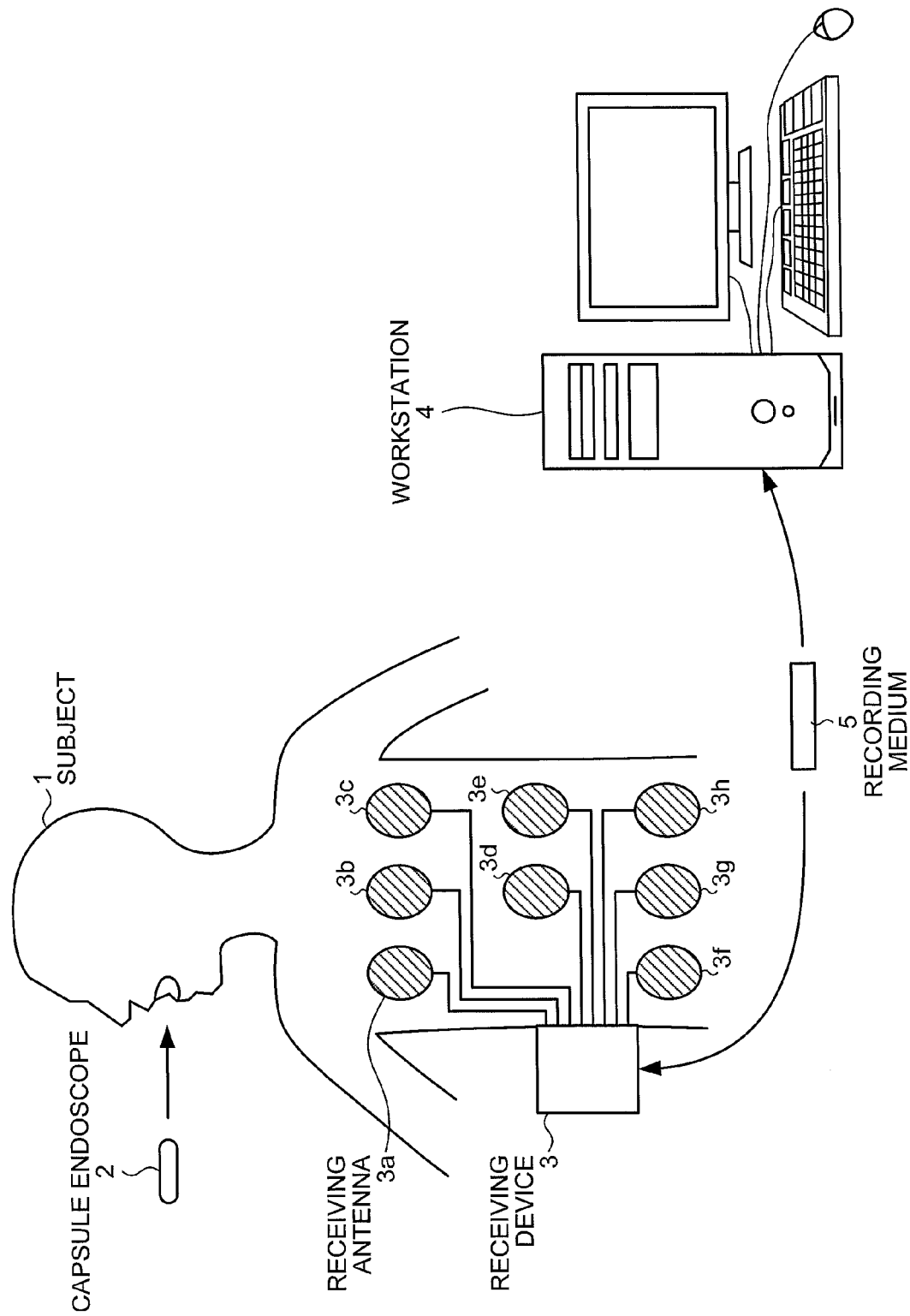
FIG. 1 is a schematic diagram illustrating a configuration example of an endoscope system using a capsule endoscope according to a first embodiment.

FIG. 1 is a schematic diagram illustrating a configuration example of an endoscope system using a capsule endoscope according to a first embodiment of the invention. As illustrated in FIG. 1, the endoscope system in the first embodiment includes a capsule endoscope 2 that captures a group of in-vivo images of a subject 1, a receiving device 3 that receives image signals wirelessly transmitted from the capsule endoscope 2, a workstation 4 that displays the group of the in-vivo images captured by the capsule endoscope 2, and a portable recording medium 5 for performing transmission and reception of data between the receiving device 3 and the workstation 4.

The capsule endoscope 2 is provided with an illumination device, an imaging unit, and a radio communication unit, in a capsule-shaped casing. The capsule endoscope 2 is introduced into organs of the subject 1 by oral ingestion or the like, and then sequentially captures in-vivo images of the subject 1 at a predetermined interval (for example, an interval of 0.5 seconds) while moving in the organs of the subject by peristaltic motion or the like. The capsule endoscope 2 illuminates photographic subjects in the organs with illumination lights such as white light, to capture images of the photographic subjects illuminated by the illumination light, that is, the in-vivo images of the subject 1. The capsule endoscope 2 wirelessly transmits image signals of the in-vivo images of the subject 1 captured as described above, the image signals being associated with imaging times or the like, to the external receiving device 3. The capsule endoscope 2 sequentially repeats the imaging operations and the wireless transmission operations of the in-vivo images in a period until the capsule endoscope is discharged outside the subject 1 after it is introduced into the organs of the subject 1.

The receiving device 3 is provided with a plurality of receiving antennas 3a to 3h distributed, for example, on a body surface of the subject 1, and receives wireless signals from the capsule endoscope 2 in the subject 1 through at least one of the plurality of receiving antennas 3a to 3h. The receiving device 3 extracts the image signals from the received wireless signals, and acquires image data of the in-vivo images included in the extracted image signals. When the in-vivo images of one frame are acquired from the capsule endoscope 2, the receiving device 3 sequentially stores the images in the recording medium 5 inserted in advance. In addition, the receiving device 3 associates each image with imaging time and exposure time data of the in-vivo image. In addition, the receiving antennas 3a to 3h of the receiving device 3 may be disposed on the body surface of the subject 1 as illustrated in FIG. 1, and may be disposed in a jacket worn on the subject 1. In addition, the number of receiving antennas of the receiving device 3 may be one or more, and is not particularly limited to eight.

The workstation 4 receives various kinds of data such as the group of the in-vivo images of the subject 1 through the recording medium 5, and displays the received various kinds of data such as the group of the in-vivo images. The recording medium 5 removed from the receiving device 3 is inserted into the workstation 4, which acquires various kinds of data such as the image data of the in-vivo images of the subject 1 by receiving the stored data of the recording medium 5. The workstation 4 displays the acquired in-vivo images on a display.

The recording medium 5 is a portable recording medium for performing transmission and reception of data between the receiving device 3 and the workstation 4 described above. The recording medium 5 has a structure in which it is attachable to and detachable from the receiving device 3 and the workstation 4 and data can be output and recorded at the time of insertion to both. The recording medium 5 records time data or the like of the group of the in-vivo images and the images image-processed by the receiving device 3 when it is inserted into the receiving device 3. Meanwhile, when the recording medium 5 removed from the receiving device 3 is inserted into the workstation 4, the workstation 4 receives the stored data (the group of the in-vivo images or the like) of the recording medium 5.

Figure 2:
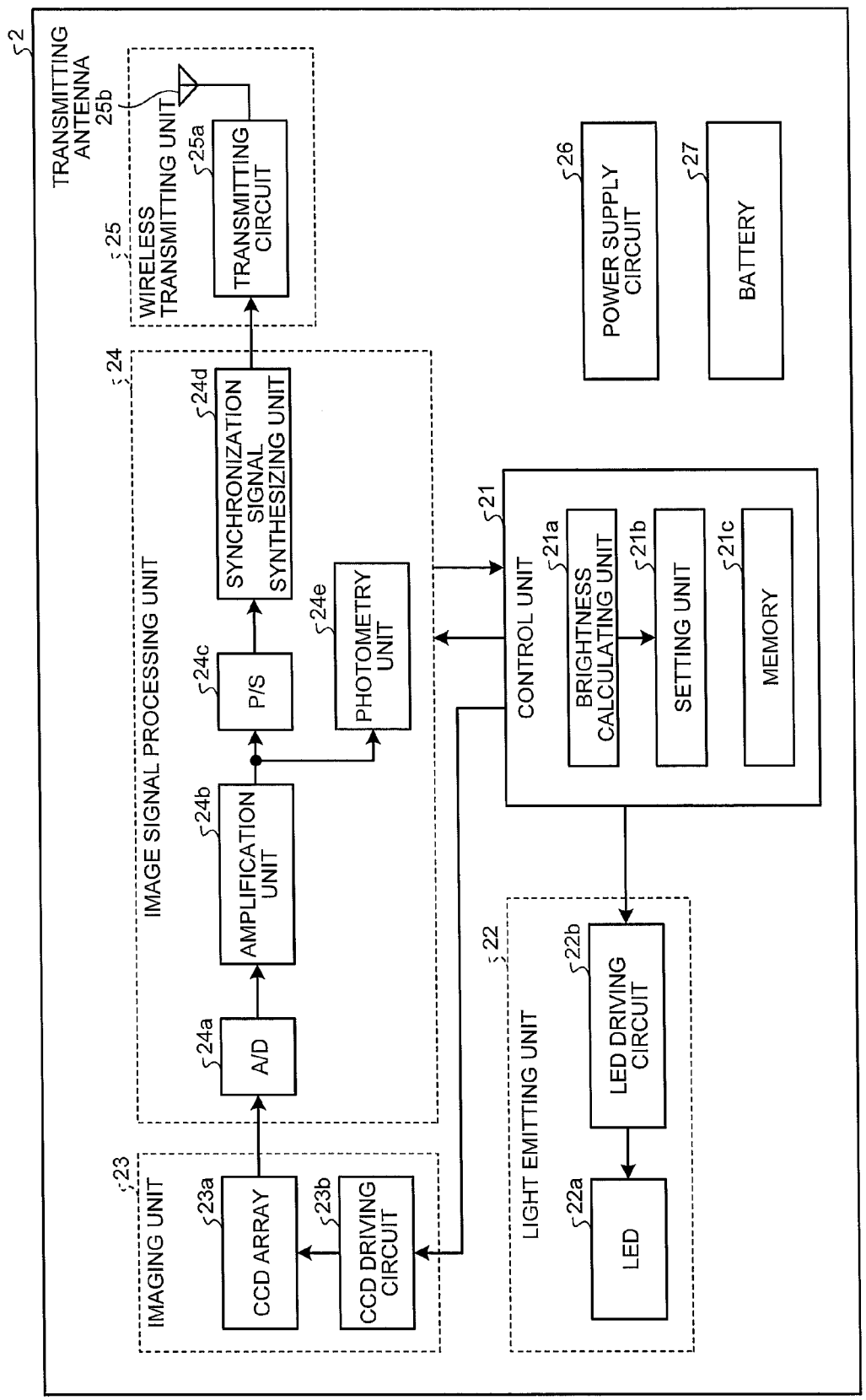
FIG. 2 is a block diagram schematically illustrating a configuration example of the capsule endoscope illustrated in FIG. 1.

Next, a structure of the capsule endoscope 2 illustrated in FIG. 1 will be described in detail. FIG. 2 is a block diagram schematically illustrating a configuration example of the capsule endoscope 2 illustrated in FIG. 1. As illustrated in FIG. 2, the capsule endoscope 2 includes a control unit 21, a light emitting unit 22, an imaging unit 23, an image signal processing unit 24, a wireless transmitting unit 25, a power supply circuit 26 that supplies driving power to the constituent units of the capsule endoscope 2, and a battery 27.

The control unit 21 controls driving of the constituent units of the capsule endoscope 2 to perform an input/output control of signals in the constituent units. The control unit 21 includes a brightness calculating unit 21a that calculates a brightness level of an image corresponding to the image signal based on the image signal output from the imaging unit 23, a setting unit 21b that sets a brightness parameter about brightness of the image based on the brightness level calculated by the brightness calculating unit 21a, and a memory 21c that stores programs used for controling the units and data such as parameters. The setting unit 21b sets, for example, the light emission time in an LED 22a of the light emitting unit 22, as the brightness parameter.

The light emitting unit 22 includes the LED 22a that emits light into the subject 1 to illuminate the inside of the subject 1, and an LED driving circuit 22b that controls a driving state of the LED 22a. In addition, a light emitting element of the light emitting unit 22 is not limited to the LED 22a, and various light emitting elements may be used.

The imaging unit 23 includes an optical system such as a lens that forms an image of reflective light from the imaging field of view, a CCD array 23a in which pixels of, for example, R, G, and B are disposed in a matrix shape, and a CCD driving circuit 23b that controls a driving state of the CCD array 23a, and captures an image of at least a part of an area illuminated by the LED 22a. Each pixel of the CCD array 23a receives light flux of the imaging field of view, and performs photoelectric conversion to output an image signal at an output level corresponding to a light reception value.

The image signal processing unit 24 performs a predetermined signal process on an analog image signal output from the imaging unit 23, and outputs a digital image signal to the wireless transmitting unit 25. The image signal processing unit 24 includes a processing circuit that performs an analog signal process such as color balance adjustment and gamma correction on the analog image signal output from the imaging unit 23, an A/D converter 24a that converts the analog image signal into a digital image signal, an amplification unit 24b that amplifies the converted digital image signal, a P/S converter 24c that modulates the digital signal output from the amplification unit 24b into a predetermined bit number of digital data and then converts the parallel data into serial data, and a synchronization signal synthesizing unit 24d that synthesizes a horizontal synchronization signal and a vertical synchronization signal in the image data converted into the serial data. In addition, the image signal processing unit 24 has a photometry unit 24e that measures a brightness value in the image signal output from the imaging unit 23 and outputs the measurement result to the control unit 21. The brightness calculating unit 21a calculates a brightness level of the image corresponding to the image signal based on the photometry result output from the photometry unit 24e.

The wireless transmitting unit 25 transmits the image signal output from the image signal processing unit 24, as a wireless signal. The wireless transmitting unit 25 includes a transmitting circuit 25a that generates and transmits the wireless signal including the image signal output from the image signal processing unit 24, and a transmitting antenna 25b that outputs the wireless signal output from the transmitting circuit 25a, to the outside, as a wireless wave.

Figure 3:
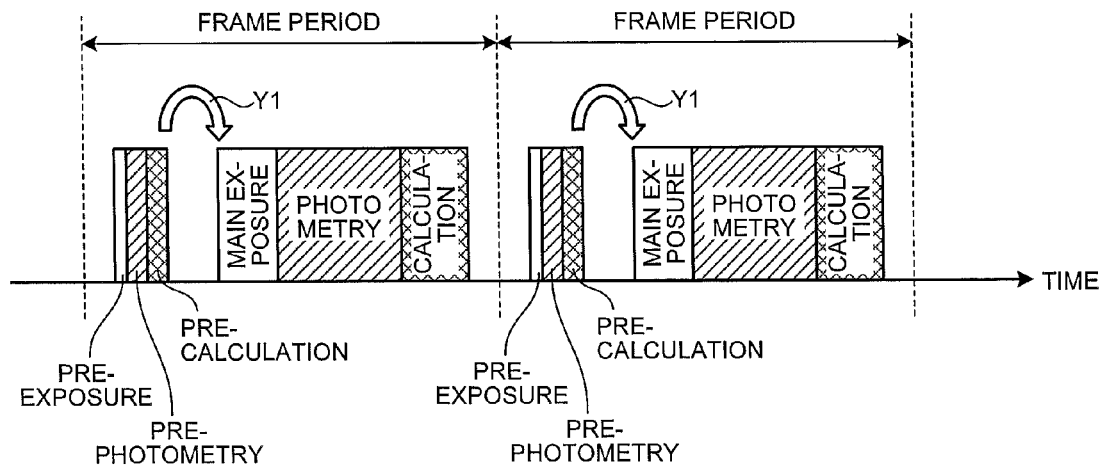
FIG. 3 is a diagram illustrating a setting of a brightness parameter in the capsule endoscope illustrated in FIG. 2.

In the capsule endoscope 2, a pre-exposure process is performed before a main exposure process for image acquisition in a frame period set to acquire one image, a brightness parameter of the image acquired in the frame period is set using the output result about the pre-exposure of a part of a plurality of pixels, and thus it is possible to acquire an image with brightness suitable for observation. Specifically, as illustrated in FIG. 3, in the same frame period before the main exposure process performed to actually acquire one image, the pre-exposure process is performed on the light emitting unit 22 and the imaging unit 23. The setting unit 21b controls the photometry unit 24e to perform a pre-photometry process of measuring a brightness value in the image signal about the pre-exposure output from the imaging unit 23. In this case, the photometry unit 24e does not perform the photometry process on the image signals of all the pixels of the CCD array 23a, but performs the photometry process only on the image signals of a part of the pixels.

The brightness calculating unit 21a calculates a brightness level of the image based on the measurement result about the pre-exposure output from the photometry unit 24e. The setting unit 21b sets a light emission time of the LED 22a of the main exposure process in this frame to acquire an image with brightness suitable for observation based on the calculation result of the brightness level of the image about the pre-exposure, and reflects the light emission time, as it is, to the main exposure process of the same frame period as indicated by an arrow Y1. As a result, the LED 22a performs the main exposure process to emit light at the light emission time set by the setting unit 21b, and then performs an imaging process performed by the CCD array 23a and a signal process in the image signal processing unit 24, and the image signals corresponding to one image are acquired. In addition, in the first embodiment, as illustrated in FIG. 3, the photometry process and the brightness level calculating process may be performed even on the image signals obtained by the imaging of the CCD array 23a after the main exposure process, or may not be performed. The photometry result of the photometry unit 24e after the exposure process is stored in the memory 21c, and is updated for each frame period.

Figure 4:
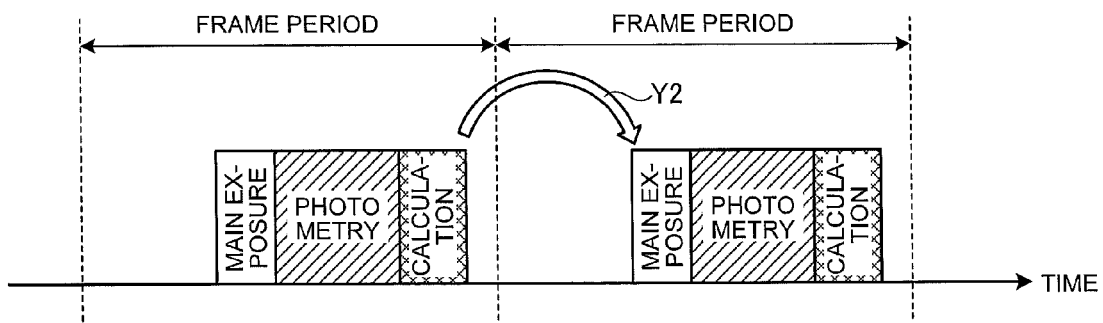
FIG. 4 is a diagram illustrating a setting of a brightness parameter in the capsule endoscope according to the prior art.

Herein, in the capsule endoscope according to the prior art, as illustrated in FIG. 4, the photometry process is performed on the image signals of all the pixels of the CCD array after the main exposure process performed in the frame period about the previous image, the brightness level of the image is calculated based on the photometry result, and the light emission time of the main exposure process in the next frame period is set and reflected as indicated by an arrow Y2. However, in the method according to the prior art, when the light emission time in the next frame period is determined based on the photometry result in the frame period about the previous image, the emission time corresponding to the brightness suitable for observation deviates from the set light emission time when the distance from a body tissue of the observation target is changed between the previous and next frame periods by movement of the capsule endoscope, and an image with brightness suitable for observation may not be obtained. In the method according to the prior art, there is a limit to a high frame rate even when trying to raise responsiveness, and it is difficult to resolve the difference between the set light emission time and the light emission time corresponding to the brightness suitable for observation.

However, in the capsule endoscope 2 according to the first embodiment, the pre-exposure process is performed in the same frame period, the light emission time is set using the photometry result about the pre-exposure of a part of the pixels, and the set light emission time is reflected, as it is, to the main exposure process of the same frame period. For this reason, according to the first embodiment, similarly to a case of achieving the high frame rate, it is possible to reduce the difference between the set light emission time and the light emission time corresponding to the brightness suitable for observation, and thus it is possible to satisfactorily acquire the image with the brightness suitable for observation. In addition, in the capsule endoscope 2, since the photometry process is not performed on all the pixels but is performed only on a part of the pixels in the pre-exposure, it is possible to set the brightness parameter in a short time, and they can be sufficiently reflected even to the main exposure process in the same frame period.

Figure 5:
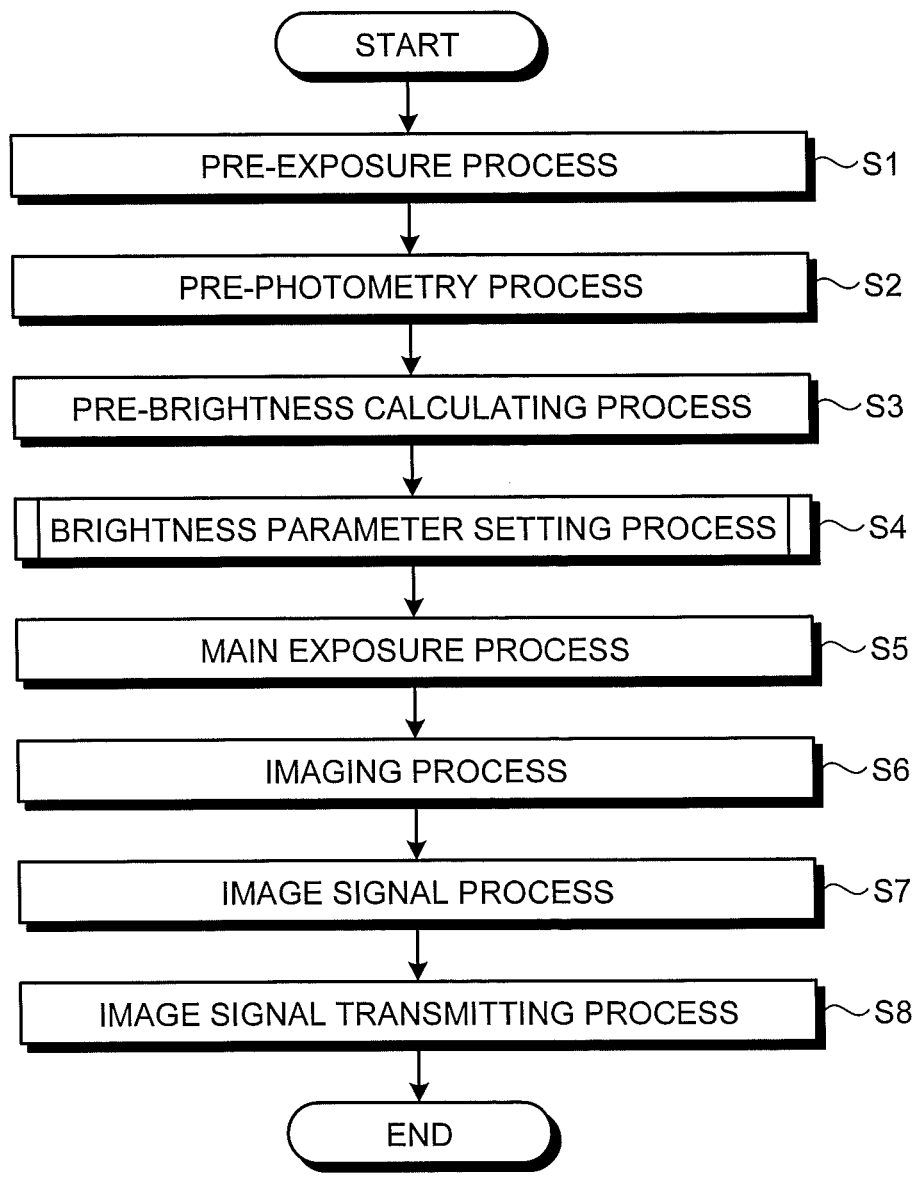
FIG. 5 is a flowchart illustrating process sequence of an image acquiring process of the capsule endoscope illustrated in FIG. 2.

Next, an image acquiring process of the capsule endoscope 2 according to the first embodiment will be described. FIG. 5 is a flowchart illustrating process sequence of an image acquiring process of the capsule endoscope 2 illustrated in FIG. 2. FIG. 5 illustrates process sequence until the capsule endoscope 2 acquires one image and transmits the image to the receiving device 3. The capsule endoscope 2 repeats processes illustrated in FIG. 5 to capture and wirelessly transmit a series of in-vivo images.

First, as illustrated in FIG. 5, in the capsule endoscope 2, the pre-exposure process of performing exposure in advance is performed before the main exposure process performed to acquire an actual image under the control of the control unit 21 (Step S1). The pre-exposure process is set to a time shorter than that of the main exposure process, the light emitting unit 22 emits light for a time shorter than that of the main exposure process, and each pixel of the CCD array 23a of the imaging unit 23 outputs the image signal at an output level corresponding to a light reception value to the image signal processing unit 24.

The photometry unit 24e performs a pre-photometry process of measuring the brightness value in the image signal output from the imaging unit 23 in the pre-exposure process and outputting the photometry result to the control unit 21 (Step S2). The photometry unit 24e does not perform the photometry process on the image signals of all the pixels of the CCD array 23a, but performs the photometry process only on the image signals of a part of the pixels.

Subsequently, the brightness calculating unit 21a performs a pre-brightness calculating process (Step S3) of calculating a brightness level of the image corresponding to the image signal, using the measurement result of a part of the pixels in the pre-exposure process output from the photometry unit 24e.

The setting unit 21b performs a brightness parameter setting process (Step S4) of setting a brightness parameter in the frame period to acquire an image with brightness suitable for observation based on the calculation result of the brightness level of the image in the pre-brightness calculating process. As the brightness parameter, the light emission time of the LED 22a is set.

Subsequently, in the capsule endoscope 2, according to the brightness parameter set in the brightness parameter setting process, in order to acquire one image, a main exposure process (Step S5) of performing a light emitting process by the light emitting unit 22, an imaging process (Step S6) of outputting the image signals by the imaging unit 23 according to the main exposure process, an image signal process (Step S7) of performing a predetermined signal process on the image signals output from the imaging unit 23 and outputting digital image signals by the image signal processing unit 24, and an image signal transmitting process (Step S8) of transmitting the image signals output from the image signal processing unit 24 as the wireless signals by the wireless transmitting unit 25 are performed, and the processes on one image are ended.

Figure 6:
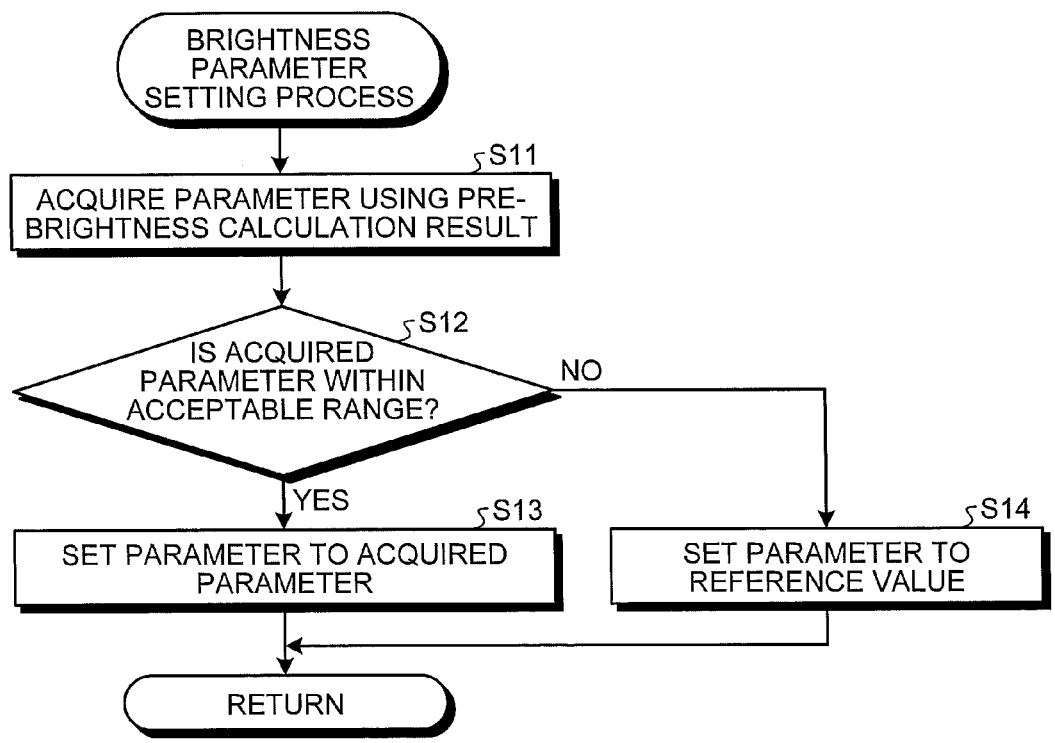
FIG. 6 is a flowchart illustrating process sequence of a brightness parameter setting process illustrated in FIG. 5.

Next, the brightness parameter setting process illustrated in FIG. 5 will be described. FIG. 6 is a flowchart illustrating process sequence of the brightness parameter setting process illustrated in FIG. 5. As illustrated in FIG. 6, the setting unit 21b acquires a value of the parameter, for example, the light emission time of the LED 22a, using the calculation result of the brightness level of the image calculated by the brightness calculating unit 21a in the pre-brightness calculating process (Step S11). For example, the memory 21c stores a relational expression between the brightness level of the image calculated in the pre-brightness calculating process and the light emission time of the LED 22a, and the setting unit 21b calculates the light emission time of the LED 22a with reference to a table in the memory 21c. In addition, the memory 21c stores a table in which the brightness levels of the image calculated in the pre-brightness calculating process are associated with the light emission times of the LED 22a corresponding to the brightness levels of the image, and the setting unit 21b acquires the light emission time of the LED 22a with reference to the table in the memory 21c.

Subsequently, the setting unit 21b determines whether or not the value of the parameter acquired in Step S11 is within a predetermined acceptable range of the parameter (Step S12). The setting unit 21b determines whether or not the light emission time of the LED 22a acquired in Step S11 is within a predetermined acceptable range of the light emission time of the LED 22a.

When it is determined that the value of the parameter acquired in Step S11 is within the predetermined acceptable range of the parameter (Yes in Step S12), the setting unit 21b sets the brightness parameter in the main exposure process, as it is, to the value of the parameter acquired in Step S11 (Step S13). When it is determined that the light emission time of the LED 22a acquired in Step S11 is within the predetermined acceptable range of the light emission time of the LED 22a, the setting unit 21b sets the light emission time of the LED 22a in the main exposure to the light emission time acquired in Step S11.

However, when it is determined that the value of the parameter acquired in Step S11 is not within the predetermined acceptable range of the parameter (No in Step S12), the setting unit 21b sets the brightness parameter in the main exposure process to a preset reference value (Step S14). For example, when the light emission time of the LED 22a acquired in Step S11 exceeds an upper limit of the acceptable range of the light emission time of the LED 22a, the setting unit 21b sets the light emission time of the LED 22a in the main exposure to an upper limit time of the acceptable range. In addition, when the light emission time of the LED 22a acquired in Step S11 is below a lower limit of the acceptable range, the setting unit 21b sets the light emission time of the LED 22a in the main exposure to a lower limit time of the acceptable range.

As described above, in the capsule endoscope 2 according to the first embodiment, by sequentially performing the processes illustrated in FIGS. 5 and 6, it is possible to appropriately set the brightness parameter while reducing the difference between the set light emission time and the light emission time corresponding to the brightness suitable for observation. That is, in the capsule endoscope 2 according to the first embodiment, a white bright image or a black dark image is decreased, it is possible to reduce the number of images until it returns to an image with suitable brightness even when there is the white bright image or the black dark image, and thus it is possible to increase the images with the brightness suitable for observation.

Figure 7:
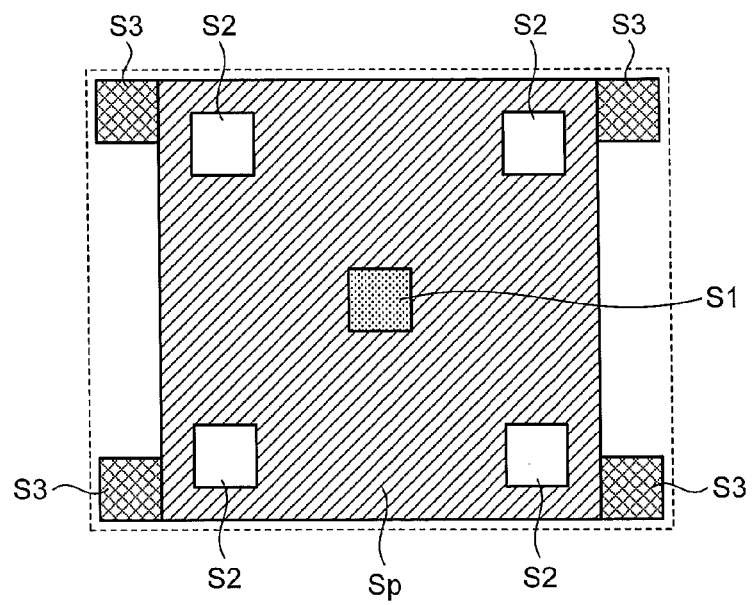
FIG. 7 is a diagram illustrating a pixel area of a CCD sensor illustrated in FIG. 2.

In addition, the pixels subjected to the photometry process in the pre-photometry process may be, for example, as illustrated in FIG. 7, an area S1 positioned substantially at the center of a pixel area Sp used to generate an image, and may be areas S2 positioned in the vicinity of corners of the pixel area Sp, in a pixel area of the CCD array 23a. In addition, the pixels subjected to the photometry process in the pre-photometry process may be areas S3 capable of receiving light from the outside in the periphery of the pixel area Sp. Of course, the pixel area where the photometry process is performed in the pre-photometry process may be any one of areas of the area S1 and areas S2, and may be a plurality of arbitrary areas of the areas S1 to S3. When the photometry results of the plurality of pixels are used, the brightness parameter may be set using an average value of the photometry results in the plurality of pixels. In addition, when the measurement results of the plurality of pixels are used, the setting unit 21b may set the brightness parameter using the maximum value or the minimum value.

In addition, in the capsule endoscope 2, the amplification unit 24b may change gains of the image signals of a part of the pixels used in the pre-photometry process for each pixel, and may output the image signals of the pixels. The setting unit 21b sets the brightness parameter using the image signals which are within the output range of the image signal processing unit 24 in the image signals amplified with gains different for each pixel by the amplification unit 24b of the image signal processing unit 24.

Figures 8, 9:
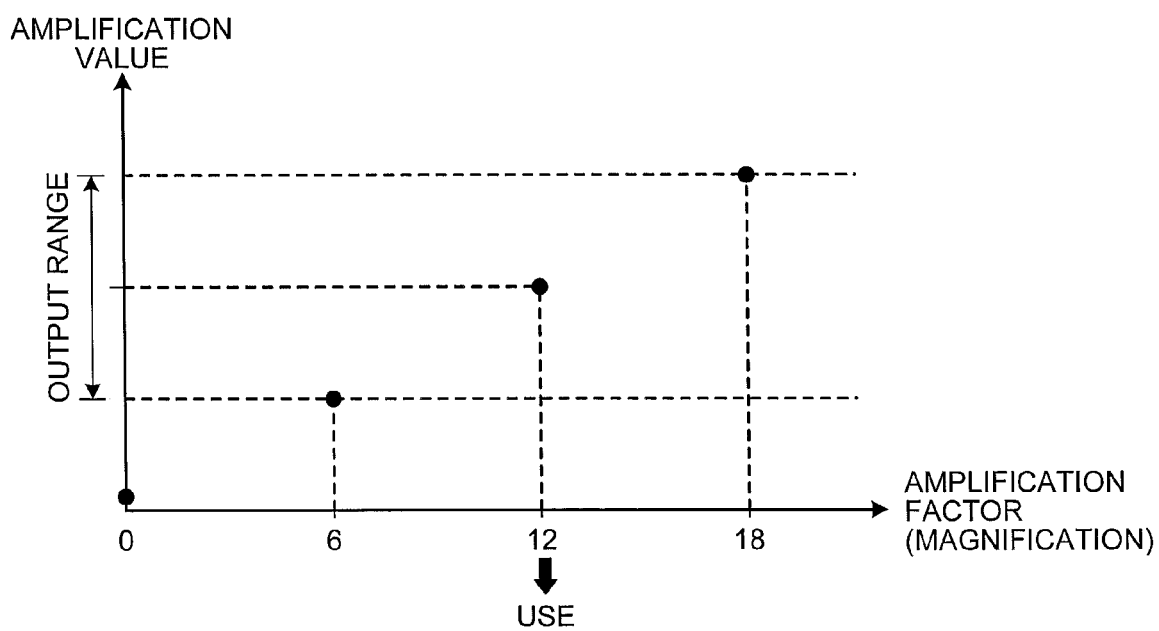
FIG. 8 is a diagram illustrating gains when an amplification unit illustrated in FIG. 2 amplifies image signals corresponding to a pre-photometry process.
FIG. 9 is a diagram illustrating an output range of an image signal processing unit illustrated in FIG. 2.

For example, as illustrated in FIG. 8, the amplification unit 24b amplifies and outputs the image signals of the pixels of the photometry targets in the pre-photometry process, at 0 magnifications, 6 magnifications, 12 magnifications, or 18 magnifications, for each pixel P. The photometry unit 24e selects image signals having values within the output range of the image signal processing unit 24 from the amplified image signals input from the amplification unit 24b, and performs the photometry process. As illustrated in FIG. 9, the photometry unit 24e does not select the image signals of 0 magnifications as an amplification factor (an example of gain) below the output range, and the image signals of 6 and 18 magnifications as the amplification factor close to the upper limit and the lower limit of the output range among the image signals within the output range, but selects the image signals of 12 magnifications as the amplification factor close to the set target value for stable output in the output range. It is possible to accurately set the parameters by selecting the image signals output as correct values in the output range without selecting the image signals having the values saturated over the output range of the image signal processing unit 24 and the image signals having the values below the output range, from the image signals amplified at the gains different for each pixel as described above.

In addition, in the first embodiment, the case where the setting unit 21b sets the light emission time of the LED 22a as the brightness parameter has been described by way of example, but, of course, the invention is not limited thereto, and the light emission intensity of the LED 22a may be set. In this case, the LED 22a performs the main exposure process of emitting light at the light emission intensity set by the setting unit 21b. In addition, the setting unit 21b may set the gain in the amplification unit 24b of the image signals output from the CCD array 23a, as the brightness parameter. In this case, the amplification unit 24b amplifies the image signals output from the CCD array 23a at the gain set by the setting unit 21b.

In addition, the setting unit 21b may set all or two of the light emission time of the LED 22a, the light emission intensity of the LED 22a, and the gain in the amplification unit 24b, as the brightness parameters.

In addition, the amplification unit 24b that amplifies the image signals after the digital conversion has been described by way of example, as the amplification unit that amplifies the image signals output from the CCD array 23a, but, of course, the invention is not limited thereto, and an amplification unit that amplifies the analog image signals before the digital conversion may be applied.

Second Embodiment

Next, a second embodiment will be described. In the second embodiment, a case of setting parameters about brightness using output results of a plurality of pixels about the main exposure performed in a frame period about a previous image, together with output results about the pre-exposure in the same frame period of a part of the pixels, will be described.

Figure 10:
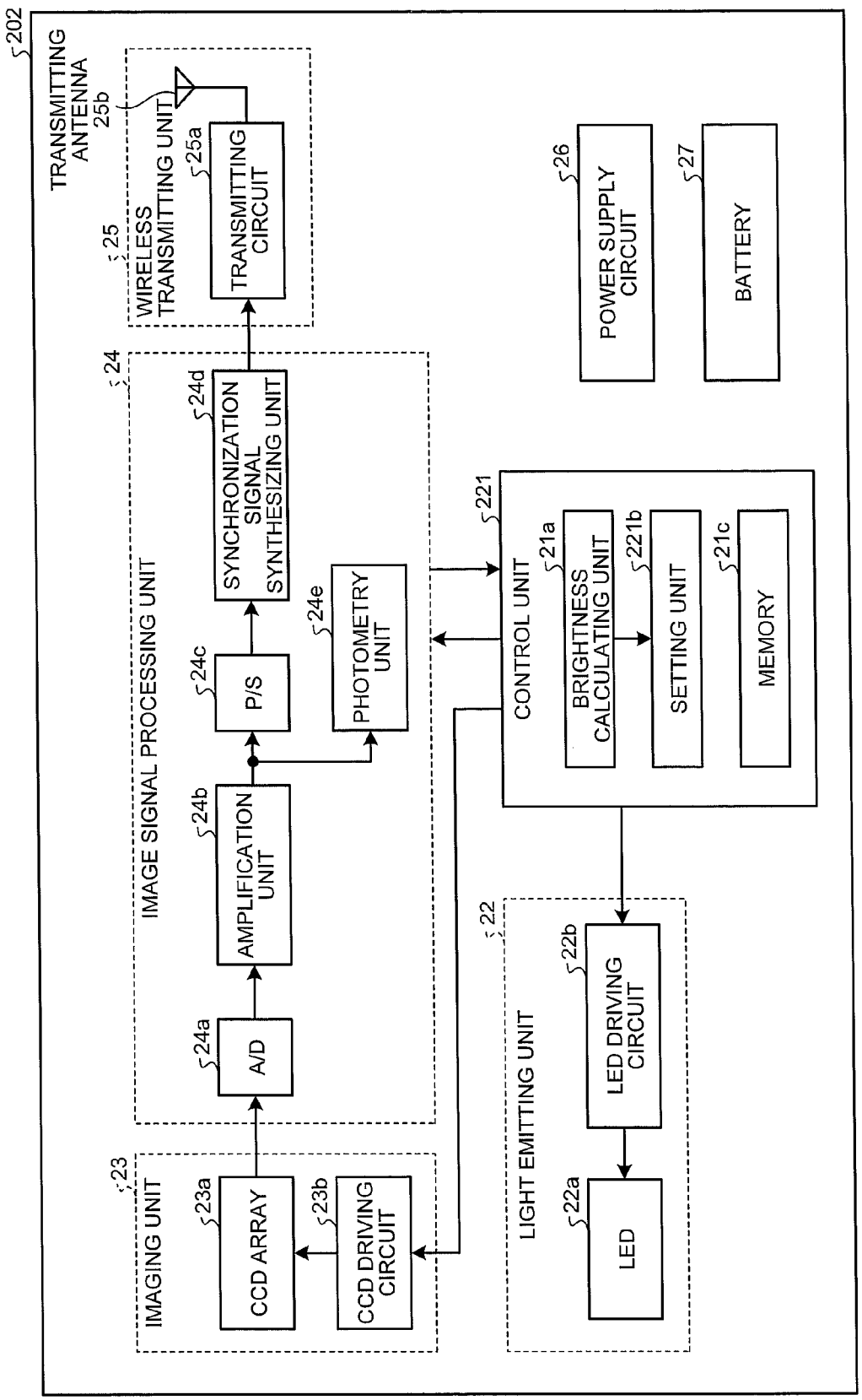
FIG. 10 is a block diagram schematically illustrating a configuration example of a capsule endoscope according to a second embodiment.

FIG. 10 is a block diagram schematically illustrating a configuration example of a capsule endoscope according to the second embodiment. As illustrated in FIG. 10, a capsule endoscope 202 according to the second embodiment has a control unit 221 instead of the control unit 21 illustrated in FIG. 2. The control unit 221 has a setting unit 221b instead of the setting unit 21b illustrated in FIG. 2.

The setting unit 221b sets a brightness parameter using output results of all the pixels in the CCD array 23a about the main exposure at the time of acquiring the previous image, together with the output results about the pre-exposure of a part of the pixels of the CCD array 23a. In addition, in the second embodiment, the photometry process and the brightness level calculating process are performed by the photometry unit 24e and the brightness calculating unit 21a, respectively, even on the image signals captured by the CCD array 23a after the main exposure process.

Setting of the brightness parameter by the setting unit 221b will be described with reference to FIGS. 11 and 12. In addition, a case where the setting unit 221b sets the light emission time of the LED 22a as the brightness parameter will be described by way of example.

Figure 11:
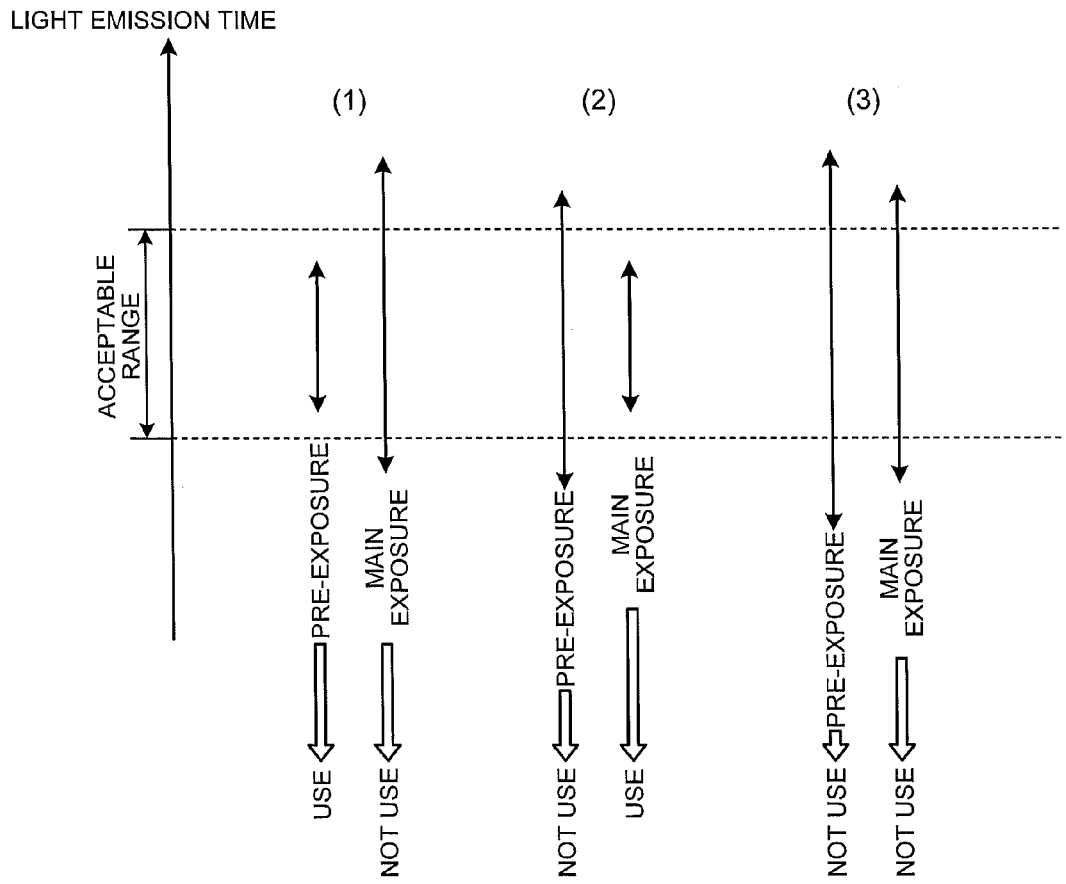
FIG. 11 is a diagram illustrating setting of a brightness parameter in the capsule endoscope illustrated in FIG. 10.
Figure 12:
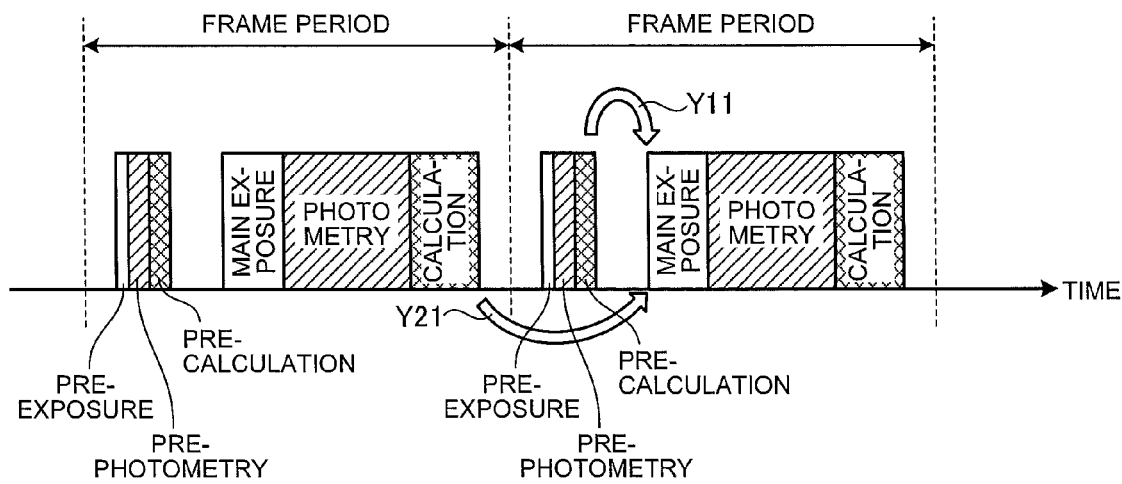
FIG. 12 is a diagram illustrating setting of a brightness parameter in the capsule endoscope illustrated in FIG. 10.

As illustrated in (1) of FIG. 11, when the light emission time of the LED 22a acquired based on the calculation result about the pre-exposure of a part of all the pixels of the CCD array 23a is within a predetermined acceptable range, the setting unit 221b reflects the acquired light emission time, as it is, to the main exposure process in the same frame period as indicated by an arrow Y11 of FIG. 12 since there is no particular problem even when the LED 22a is emitted at the light emission time. In this case, the photometry results of all the pixels about the main exposure at the time of acquiring the previous image are not used. In addition, the calculation result described herein represents the brightness level of the image calculated by the brightness calculating unit 21a based on the photometry result about the exposure process output from the photometry unit 24e.

Meanwhile, as illustrated in (2) of FIG. 11, when the light emission time of the LED 22a acquired based on the calculation results about the pre-exposure of a part of all the pixels of the CCD array 23a is out of the predetermined acceptable range, the light emission time of the LED 22a acquired based on the calculation results about the pre-exposure of a part of the pixels is not used since it is not preferable that the LED 22a emits light at the light emission time out of the acceptable range. The setting unit 221b acquires the light emission time of the LED 22a based on the photometry results of all the pixels about the main exposure at the time of acquiring the previous image. Thereafter, when the light emission time of the LED 22a acquired based on the photometry results of all the pixels about the main exposure at the time of acquiring the previous image is within the predetermined acceptable range, the setting unit 221b reflects the light emission time to the main exposure process in the same frame period as indicated by an arrow Y21 of FIG. 12.

Meanwhile, as illustrated in (3) of FIG. 11, when the light emission time of the LED 22a acquired based on the photometry results of all the pixels about the main exposure at the time of acquiring the previous image is out of the predetermined acceptable range, the setting unit 221b sets the light emission time of the LED 22a to a predetermined reference time without using any light emission time.

As described above, in the capsule endoscope 202 according to the second embodiment, when the values of the parameters acquired using the photometry results about the pre-exposure of a part of the pixels are not appropriate, it is possible to further satisfactorily acquire the image with the brightness suitable for observation using the parameters acquired with high precision based on the photometry results of all the pixels about the main exposure at the time of acquiring the previous image.

Figure 13:
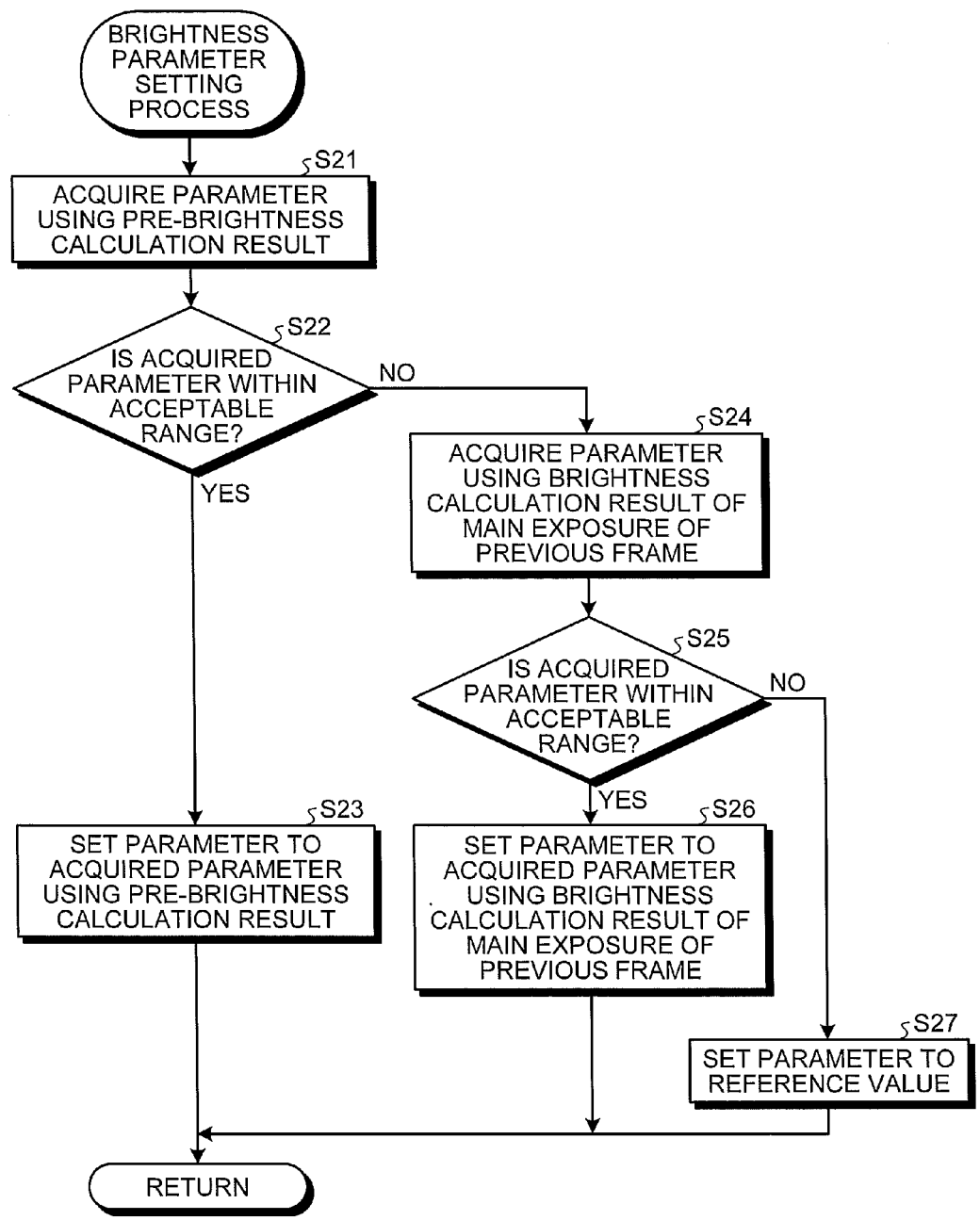
FIG. 13 is a flowchart illustrating each process sequence of a brightness parameter setting process of the capsule endoscope illustrated in FIG. 10.

Next, an image acquiring process of the capsule endoscope 202 according to the second embodiment will be described. The capsule endoscope 202 acquires one image by performing the same processes as the processes illustrated in FIG. 5, and transmits the image to the receiving device 3. Herein, a brightness parameter setting process in the second embodiment will be described with reference to FIG. 13. FIG. 13 is a flowchart illustrating each process sequence of the brightness parameter setting process of the capsule endoscope 202 illustrated in FIG. 10.

As illustrated in FIG. 13, similarly to Step S11 illustrated in FIG. 6, the setting unit 221b acquires the value of the parameter, for example, the light emission time of the LED 22a using the calculation result of the brightness level of the image calculated by the brightness calculating unit 21a in the pre-brightness calculating process (Step S21). Subsequently, similarly to Step S12 illustrated in FIG. 6, the setting unit 221b determines whether or not the value of the parameter acquired in Step S21 is within a predetermined acceptable range of the parameter (Step S22).

When it is determined that the value of the parameter acquired in Step S21 is within the predetermined acceptable range (Yes in Step S22), the setting unit 221b sets the brightness parameter in the main exposure process to the value of the parameter acquired using the pre-brightness calculation result acquired in Step S21 (Step S23).

Meanwhile, when it is determined that the value of the parameter acquired in Step S21 is not within the predetermined acceptable range of the parameter (No in Step S22), the setting unit 221b acquires the value of the parameter using the calculation result of the brightness of the image based on the photometry results of all the pixels in the main exposure performed in the frame period about the previous image subjected to photometry by the photometry unit 24e (Step S24). In addition, the calculation result represents the brightness level of the image calculated by the brightness calculating unit 21a based on the photometry result about the exposure process output from the photometry unit 24e.

Subsequently, the setting unit 221b determines whether or not the value of the parameter acquired in Step S24 is within a predetermined acceptable range of the parameter (Step S25).

When it is determined that the value of the parameter acquired in Step S24 is within the predetermined acceptable range of the parameter (Yes in Step S25), the setting unit 221b sets the brightness parameter in the main exposure process to the value of the parameter acquired using the brightness calculation result about the main exposure performed in the frame period about the previous image acquired in Step S24 (Step S26).

Meanwhile, when it is determined that the value of the parameter acquired in Step S24 is not within the predetermined acceptable range of the parameter (No in Step S25), the setting unit 221b sets the brightness parameter in the main exposure process to a preset reference value (Step S27).

As described above, in the capsule endoscope 202 according to the second embodiment, by sequentially performing the processes illustrated in FIG. 13, it is possible to further satisfactorily acquire the image with the brightness suitable for observation.

In addition, the processes illustrated in FIG. 13 represent an example of process sequence of the brightness parameter setting process in the second embodiment, and the brightness parameter setting process in the second embodiment is not limited thereto. For example, the setting unit 221b may acquire an average value between the value of the parameter acquired based on the calculation result in the pre-brightness calculating process and the value of the parameter acquired based on the photometry result of the main exposure performed in the frame period about the previous image, to set the average value to the brightness parameter. In addition, the setting unit 221b may acquire a difference between the value of the parameter acquired based on the calculation result in the pre-brightness calculating process and a predetermined reference value and a difference between the value of the parameter acquired based on the photometry result of the main exposure performed in the frame period about the previous image and a predetermined reference value, and may set the value of the smaller difference as the brightness parameter. In addition, the setting unit 221b may set a value within a predetermined range of a difference between the value of the parameter acquired based on the calculation result in the pre-brightness calculating process and a predetermined reference value and a difference between the value of the parameter acquired based on the photometry result of the main exposure performed in the frame period about the previous image and a predetermined reference value, as the brightness parameter.

Third Embodiment

Next, a third embodiment will be described. In the third embodiment, a case of selecting the photometry result used to set the brightness parameter between the photometry result in the pre-photometry process and the photometry result of the main exposure performed in the frame period about the previous image, according to a movement state of the capsule endoscope, will be described.

Figure 14:
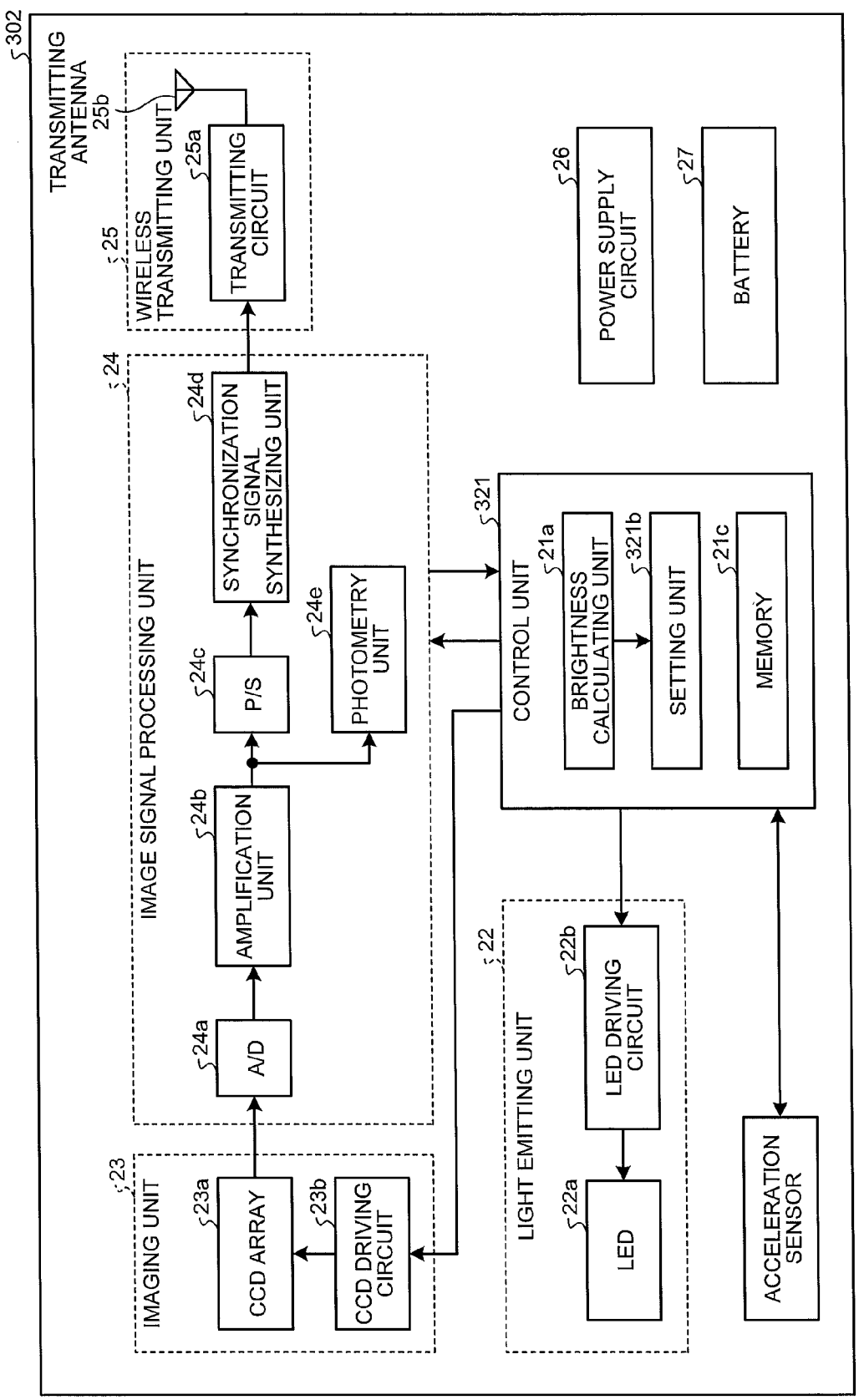
FIG. 14 is a block diagram schematically illustrating a configuration example of a capsule endoscope according to a third embodiment.

FIG. 14 is a block diagram schematically illustrating a configuration example of a capsule endoscope according to the third embodiment. As illustrated in FIG. 14, a capsule endoscope 302 according to the third embodiment has a control unit 321 instead of the control unit 21 illustrated in FIG. 2, and further includes an acceleration sensor 328 that detects acceleration of the capsule endoscope 302 and outputs the acceleration to the control unit 321, as compared with the capsule endoscope 2 illustrated in FIG. 2. The acceleration sensor 328 has a function of detecting a movement state of the capsule endoscope 302.

The control unit 321 has a setting unit 321b instead of the setting unit 21b illustrated in FIG. 2. The setting unit 321b selects any of the output result about the pre-exposure and the output result of the plurality of pixels about the main exposure at the time of acquiring the previous image, according to the detection result of the acceleration sensor 328, and sets the brightness parameter.

Figure 15:
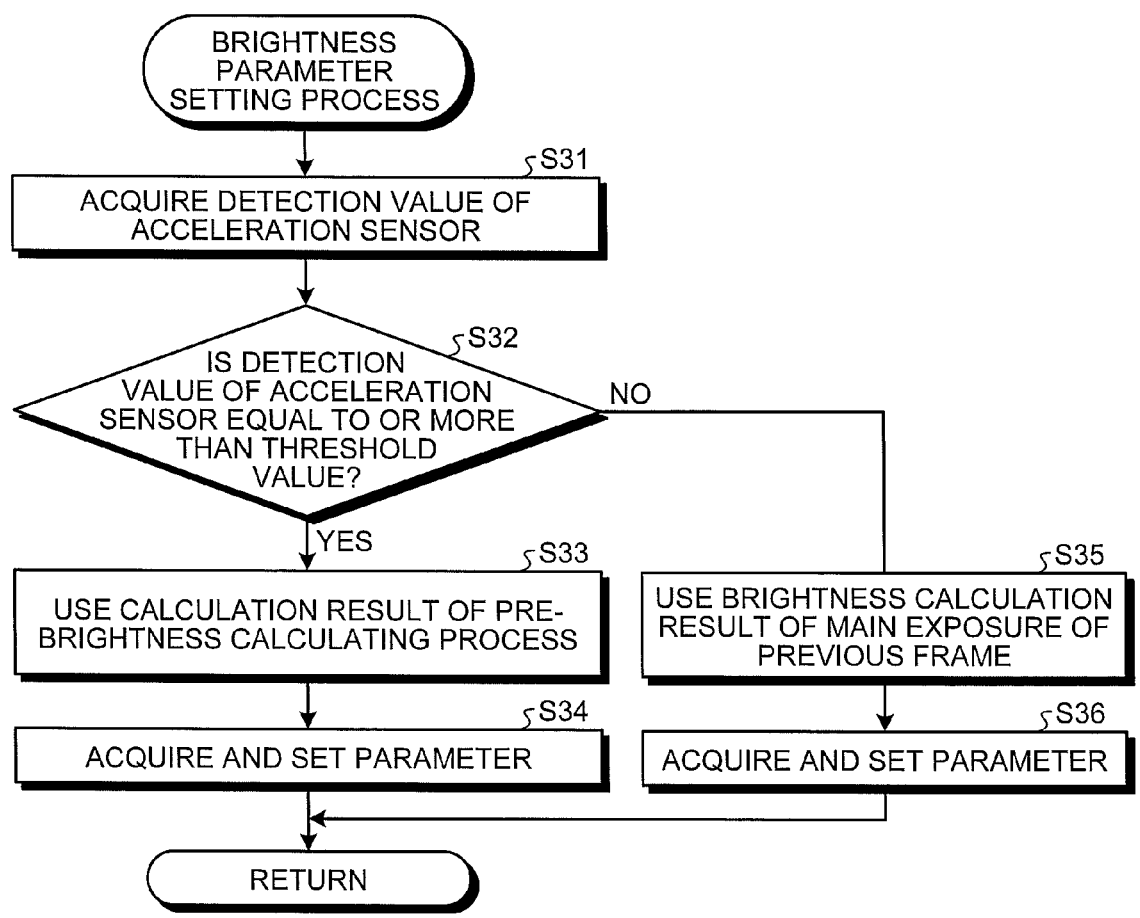
FIG. 15 is a flowchart illustrating each process sequence of a brightness parameter setting process of the capsule endoscope illustrated in FIG. 14.

Next, the image acquiring process of the capsule endoscope 302 according to the third embodiment will be described. The capsule endoscope 302 acquires one image by performing the same processes as the processes illustrated in FIG. 5, and transmits the image to the receiving device 3. Herein, the brightness parameter setting process in the third embodiment will be described with reference to FIG. 15. FIG. 15 is a flowchart illustrating each process sequence of the brightness parameter setting process of the capsule endoscope 302 illustrated in FIG. 14.

First, as illustrated in FIG. 15, the setting unit 321b acquires a detection value of the acceleration sensor 328 (Step S31). Subsequently, the setting unit 321b determines whether or not the acquired detection value of the acceleration sensor 328 is equal to or more than a predetermined threshold value (Step S32). The threshold value is set based on a movement speed when the capsule endoscope 302 moves between the previous and next frame periods by a distance having no interference to acquire the image with the brightness suitable for observation.

When the setting unit 321b determines that the acquired detection value of the acceleration sensor 328 is equal to or more than the predetermined threshold value (Yes in Step S32), the case corresponds to a case where the capsule endoscope 302 drastically moves from the position in the frame period about the previous image. Accordingly, when the brightness parameter corresponding to the frame period is set using the photometry results of all the pixels in the main exposure performed in the frame period about the previous image, a difference between the set light emission time and the light emission time corresponding to the brightness suitable for observation occurs, and it is difficult to acquire the image with the brightness suitable for observation. For this reason, in order to reduce the difference between the set light emission time and the light emission time corresponding to the brightness suitable for observation, the setting unit 321b does not use the photometry result of all the pixels in the main exposure performed in the frame period about the previous image but uses the calculation result in the pre-brightness calculating process (Step S33), and acquires and sets the brightness parameter corresponding to the calculation result in the pre-brightness calculating process (Step S34). In addition, the calculation result described herein represents the brightness level of the image calculated by the brightness calculating unit 21a based on the photometry result about the exposure process output from the photometry unit 24e.

Meanwhile, when the setting unit 321b determines that the acquired detection value of the acceleration sensor 328 is not equal to or more than the predetermined threshold value (No in Step S32), the case corresponds to a case where the capsule endoscope 302 does not move so much from the position in the frame period about the previous image. Accordingly, even when the brightness parameter corresponding to the frame period is set using the photometry results of all the pixels in the main exposure performed in the frame period about the previous image, an influence of difference in time is small, and it is possible to sufficiently acquire the image with the brightness suitable for observation. In addition, since the photometry results of all the pixels in the main exposure performed in the frame period about the previous image is used, it is possible to set the brightness parameter corresponding to the frame period with high precision. For this reason, the setting unit 321b does not use the calculation result in the pre-brightness calculating process but uses the calculation result of the brightness of the image based on the photometry results of all the pixels in the main exposure performed in the frame period about the previous image (Step S35), and acquires and sets the brightness parameter corresponding to the calculation result (Step S36).

As described above, in the third embodiment, the used photometry result is selected between the photometry result in the pre-photometry process and the photometry result of the main exposure performed in the frame period about the previous image, according to the detection result of the acceleration sensor 328, and thus it is possible to appropriately acquire the image with the brightness suitable for observation according to the movement state of the capsule endoscope 302.

In addition, the first to third embodiments, a so-called monocular capsule endoscope has been described, but, of course, the invention may be applied to a capsule endoscope having a plurality of light emitting units 22 and imaging units 23. In this case, the light emitting units 22 and the imaging units 23 each perform the pre-exposure process for each frame, and each brightness parameter may be set based on the output result from each imaging unit 23.

As described above, according to the first to third embodiments, the pre-exposure is performed in the same frame period, the brightness parameter about the brightness of the image is set using the photometry results about the pre-exposure of a part of the pixels, the set parameter is reflected, as it is, in the same frame period, and thus it is possible to acquire the image with the brightness suitable for observation.

The first to third embodiments described above and modification examples thereof are merely examples for embodying the invention, and the invention is not limited thereto. From the description, it is obvious that the invention may be variously modified according to specifications, and may realize other various embodiments in the scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope for being introduced into a living body, comprising:
    a light emitting unit that emits light;
    an imaging unit that has a plurality of pixels outputting image signals at an output level corresponding to a light reception value and captures an image;
    an image signal processing unit that processes the image signals output from the imaging unit; and
    a setting unit that controls the light emitting unit and the imaging unit to perform pre-exposure of the plurality of pixels before a main exposure process for image acquisition in a frame period set to acquire one image, thereafter acquires at least one of a light emission time, a light emission intensity and a gain of the image signal processing unit based on a brightness level obtained by a photometry process on the image signals of a part of the plurality of pixels of which the pre-exposure has been performed, and sets the acquired at least one of the light emission time, the light emission intensity and the gain of the image signal processing unit as at least one of a light emission time, a light emission intensity and a gain of the image signal processing unit for the main exposure process in the frame period based on the acquired at least one of the light emission time, the light emission intensity and the gain of the image signal processing unit,
    wherein the setting unit sets the acquired at least one of the light emission time, the light emission intensity and the gain of the image signal processing unit as at least one of the light emission time, the light emission intensity and the gain of the image signal processing unit for the main exposure process in the frame period when the acquired at least one of the light emission time, the light emission intensity and the gain of the image signal processing unit is within a predetermined acceptable range,
    the setting unit, when the acquired at least one of the light emission time, the light emission intensity and the gain of the image signal processing unit is not within the predetermined acceptable range, compares, with the predetermined acceptable range, at least one of a light emission time, a light emission intensity and a gain of the image signal processing unit acquired based on a brightness level obtained by a photometry process in a previous frame period which is one frame before the frame period and sets the at least one of the light emission time, the light emission intensity and the gain of the image signal processing unit acquired based on the brightness level obtained by the photometry process in the previous frame period as at least one of the light emission time, the light emission intensity and the gain of the image signal processing unit for the main exposure process in the frame period when the at least one of the light emission time, the light emission intensity and the gain of the image signal processing unit acquired based on the brightness level obtained by the photometry process in the previous frame period is within the predetermined acceptable range, and
    at least one of the light emitting unit and the image signal processing unit performs a process related to an acquisition process of the image acquired in the frame period, in accordance with the at least one of the light emission time, the light emission intensity and the gain of the image signal processing unit set by the setting unit.

2. The capsule endoscope according to claim 1, wherein the image signal processing unit amplifies the image signals output from the part of pixels in the pre-exposure, at gains different for each pixel, and the setting unit sets the at least one of the light emission time, the light emission intensity and the gain of the image signal processing unit using image signals within the output range of the image signal processing unit, in the image signals amplified at the gains different for each pixel by the image signal processing unit.

3. The capsule endoscope according to claim 1, wherein the setting unit sets one of a predetermined light emission time, a predetermined light emission intensity and a predetermined gain of the image signal processing unit as one of a light emission time, a light emission intensity and a gain of the image signal processing unit for the main exposure process in the frame period when the acquired at least one of the light emission time, the light emission intensity and the gain of the image signal processing unit is not within the predetermined acceptable range and when the at least one of the light emission time, the light emission intensity and the gain of the image signal processing unit acquired based on the brightness level obtained by the photometry process in the previous frame period is not within the predetermined acceptable range.

\* \* \* \* \*